US012770378B2

(12) United States Patent
Chen et al.

(10) Patent No.: US 12,770,378 B2
(45) Date of Patent: Oct. 20, 2026

(54) MEDICAL IMAGING ANALYSIS USING SELF-SUPERVISED LEARNING

(71) Applicant: Bristol-Myers Squibb Company, Princeton, NJ (US)

(72) Inventors: Zekai Chen, Gaithersburg, MD (US); Kevin Alex Brown, Drexel Hill, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 632 days.

(21) Appl. No.: 18/304,330

(22) Filed: Apr. 20, 2023

(65) Prior Publication Data

US 2023/0410483 A1 Dec. 21, 2023

Related U.S. Application Data

(60) Provisional application No. 63/333,495, filed on Apr. 21, 2022.

(51) Int. Cl.
*G06V 10/774* (2022.01)
*G06N 3/0455* (2023.01)
(Continued)

(52) U.S. Cl.
CPC ....... *G06V 10/7753* (2022.01); *G06N 3/0455* (2023.01); *G06N 3/0895* (2023.01);
(Continued)

(58) Field of Classification Search
CPC .... G06V 10/774; G06V 10/776; G06V 10/26; G06T 7/00; G06T 9/00; G06N 3/0455; G06N 3/0895
See application file for complete search history.

(56) References Cited

U.S. PATENT DOCUMENTS

2019/0205606 A1* 7/2019 Zhou .......................... G06T 7/11
2020/0311911 A1* 10/2020 Poole ..................... G06N 3/045
(Continued)

FOREIGN PATENT DOCUMENTS

WO 2019167884 A1 9/2019
WO 2020243756 A1 12/2020
(Continued)

OTHER PUBLICATIONS

Cai Zhiyuan'et al:"Uni4Eye: Unified 2D and 3D Self-supervised Pre-training via Masked Image Modeling Transformer for Ophthalmic Image Classification", Mar. 9, 2022 (Mar. 9, 2022), XP093064865, DOI: 10.48550/arxiv.2203.04614 Retrieved from the Internet: URL:https://arxiv.org/pdf/2203.04614.pdf [retrieved on Jul. 18, 2023] the whole document.
(Continued)

*Primary Examiner* — Akwasi M Sarpong
*Assistant Examiner* — Michael L Burleson
(74) *Attorney, Agent, or Firm* — Honigman LLP; Grant Griffith

(57) ABSTRACT

A method includes obtaining a first training data set including unannotated multi-dimensional medical images and executing a self-supervised masked image modeling (MIM) training process to pre-train an image encoder on the first training data set. The method also includes obtaining a second training data set that includes annotated multi-dimensional medical images. Here, each annotated multi-dimensional medical image includes a plurality of image voxels each paired with a corresponding ground-truth label indicating a class the corresponding image voxel belongs to. The method also includes executing a supervised training process to train an image analysis model on the second training data set to teach the image analysis model to learn how to predict the corresponding ground-truth labels for the
(Continued)

plurality of image voxels of each annotated multi-dimensional medical image. The image analysis model incorporates the pre-trained image encoder.

16 Claims, 13 Drawing Sheets

(51) Int. Cl.

| | |
|---|---|
| ***G06N 3/0895*** | (2023.01) |
| ***G06T 7/00*** | (2017.01) |
| ***G06T 7/11*** | (2017.01) |
| ***G06T 9/00*** | (2006.01) |
| ***G06V 10/26*** | (2022.01) |
| ***G06V 10/776*** | (2022.01) |
| ***G16H 30/20*** | (2018.01) |

(52) U.S. Cl.

CPC .............. *G06T 7/0012* (2013.01); *G06T 7/11* (2017.01); *G06T 9/002* (2013.01); *G06V 10/26* (2022.01); *G06V 10/776* (2022.01); *G06T 2200/04* (2013.01); *G06T 2207/10081* (2013.01); *G06T 2207/10088* (2013.01); *G06T 2207/20021* (2013.01); *G06T 2207/20081* (2013.01); *G06T 2207/20084* (2013.01); *G06T 2207/30096* (2013.01); *G06V 2201/03* (2022.01); *G16H 30/20* (2018.01)

(56) References Cited

U.S. PATENT DOCUMENTS

| | | | | |
|---|---|---|---|---|
| 2020/0364570 | A1 | 11/2020 | Kitamura | |
| 2021/0343014 | A1* | 11/2021 | Haghighi | G06V 10/82 |
| 2021/0401392 | A1* | 12/2021 | Bengtsson | G16H 30/40 |
| 2022/0067579 | A1 | 3/2022 | Choi et al. | |
| 2022/0198254 | A1* | 6/2022 | Dalli | G06N 3/094 |
| 2022/0309811 | A1* | 9/2022 | Haghighi | G06V 10/764 |
| 2023/0215147 | A1* | 7/2023 | Li | G06V 10/761 382/157 |
| 2023/0306723 | A1* | 9/2023 | Ma | G06V 10/776 |
| 2023/0368888 | A1* | 11/2023 | Kamen | A61B 5/7267 |
| 2024/0177838 | A1* | 5/2024 | Liu | G06V 10/7715 |
| 2025/0265717 | A1* | 8/2025 | Janisch | G06T 7/187 |

FOREIGN PATENT DOCUMENTS

| | | |
|---|---|---|
| WO | 2021154878 A1 | 8/2021 |
| WO | 2022049901 A1 | 3/2022 |

OTHER PUBLICATIONS

Sara Atito et al: “SIT: Self-supervised vision Transformer”,arxiv.org, Cornell University Library, 201 Olin Library Cornell University Ithaca, NY 14853, Nov. 14, 2021(Nov. 14, 2021), XP091087348, the whole document.

International Search Report and Written opinion relating to application No. PCT/2023/019323, dated Jul. 26, 2023.

Hangbo Bao et al. “BEIT: Pre-Training of Image Transformers”. Retrieved from arXiv.org (https://arxiv.org/pdf/2106.08254v2.pdf). Sep. 3, 2022.

Zhenda Xie et al. “SimMIM: a Simple Framework for Masked Image Modeling”. arXv.org ( https://arxiv.org/pdf/2111.09886.pdf). Apr. 17, 2022.

Japanese Office Action for Application 2024-561905 dated Sep. 30, 2025.

Koga, [BEIT; BERT Pre-Training of Image Transformers] A detailed explanation of the BEIT model for self-supervised pre-training!, DeepSquare Media [online], Jun. 28, 2021, [retrieved Sep. 12, 2025], Available at <https://deepsquare.jp/2021/06/beit/>.

* cited by examiner

| Methods | Backbones | Multi-Organ Sementation | | | | | | | | | | | | | Avg. ↑ |
|---|---|---|---|---|---|---|---|---|---|---|---|---|---|---|---|
| | | Spleen | RKid | LKid | Gall | Eso | Liv | Sto | Aor | IVC | Veins | Pan | RAG | LAG | |
| Sup. baseline our impl. | ViT3D-B | 0.8902 | 0.8926 | 0.8769 | 0.4763 | 0.4891 | 0.9447 | 0.7475 | 0.8207 | 0.773 | 0.6175 | 0.6442 | 0.5663 | 0.4699 | 0.7084 |
| | ViT3D-L | 0.8993 | 0.9018 | 0.3859 | 0.4813 | 0.4942 | 0.9643 | 0.7653 | 0.8292 | 0.7810 | 0.6239 | 0.6508 | 0.5721 | 0.4749 | 0.7167 |
| | Swin3D-T | 0.8638 | 0.8661 | 08508 | 0.4622 | 0.4746 | 0.9166 | 0.7255 | 0.7963 | 0.7500 | 0.5992 | 0.6252 | 0.5496 | 0.4560 | 0.6874 |
| | Swin3D-S | 0.8792 | 0.8815 | 0.8661 | 0.4704 | 0.4833 | 0.9333 | 0.7383 | 0.8107 | 0.7635 | 0.6099 | 0.6363 | 0.5594 | 0.4641 | 0.6997 |
| | Swin3D-B | 0.8852 | 0.8876 | 0.8721 | 0.4737 | 0.4864 | 0.9395 | 0.7434 | 0.8162 | 0.7687 | 0.6141 | 0.6407 | 0.5632 | 0.4673 | 0.7045 |
| | VAN3D-S | 0.8572 | 0.8595 | 0.8444 | 0.4587 | 0.4711 | 0.9098 | 0.7198 | 0.7904 | 0.744 | 0.5946 | 0.6204 | 0.5454 | 0.4525 | 0.6822 |
| | VAN3D-B | 0.8813 | 0.8837 | 0.8682 | 0.4716 | 0.4843 | 0.9354 | 0.7401 | 0.8126 | 0.7653 | 0.6114 | 0.6379 | 0.5607 | 0.4653 | 0.7014 |
| SimCLR | ViT3D-B | 0.9110 | 0.9135 | 0.8974 | 0.4875 | 0.5007 | 0.9669 | 0.7650 | 0.8399 | 0.7912 | 0.6320 | 0.6594 | 0.5795 | 0.4810 | 0.7249 |
| | ViT3D-L | 0.9279 | 0.9304 | 0.9141 | 0.4965 | 0.5099 | 0.9849 | 0.7792 | 0.8556 | 0.8058 | 0.6437 | 0.6716 | 0.5904 | 0.4899 | 0.7385 |
| MAE | ViT3D-B | 0.9488 | 0.9502 | 0.9341 | 0.5066 | 0.521 | 0.9863 | 0.7969 | 0.8742 | 0.8248 | 0.6589 | 0.6868 | 0.6052 | 0.5010 | <u>0.7534</u> |
| | ViT3D-L | 0.9541 | 0.9566 | 0.9399 | 0.5105 | 0.5243 | 0.9878 | 0.8012 | 0.8797 | 0.8285 | 0.6618 | 0.6905 | 0.6070 | 0.5037 | <u>0.7574</u> |
| SimMIM | ViT3D-B | 0.9520 | 0.9545 | 0.9378 | 0.5194 | 0.5232 | 0..9875 | 0.7995 | 0.8776 | 0.8267 | 0.6605 | 0.6890 | 0.6076 | 0.5126 | <u>0.7575</u> |
| | ViT3D-L | 0.9556 | 0.9582 | 0.9414 | 0.5206 | 0.5352 | 0.9898 | 0.8025 | 0.8811 | 0.8298 | 0.6649 | 0.6916 | 0.6088 | 0.5045 | **0.7603** |
| | Swin3D-T | 0.9157 | 0.9182 | 0.9021 | 0.4900 | 0.5032 | 0.9719 | 0.7690 | 0.8443 | 0.7952 | 0.6352 | 0.6628 | 0.5826 | 0.4834 | 0.7288 |
| | Swin3D-S | 0.9319 | 0.9344 | 0.9181 | 0.4987 | 0.5121 | 0.9891 | 0.7826 | 0.8593 | 0.8093 | 0.6465 | 0.6745 | 0.5929 | 0.4920 | 0.7416 |
| | Swin3D-B | 0.9387 | 0.9413 | 0.9248 | 0.5023 | 0.5159 | 0.9963 | 0.7883 | 0.8656 | 0.8152 | 0.6512 | 0.6794 | 0.5973 | 0.4956 | 0.7471 |
| | VAN3D-S | 0.9090 | 0.9115 | 0.8955 | 0.4864 | 0.4995 | 0.9648 | 0.7634 | 0.8382 | 0.7894 | 0.6306 | 0.6579 | 0.5784 | 0.4799 | 0.7234 |
| | VAN3D-B | 0.9350 | 0.9757 | 0.9211 | 0.5003 | 0.5138 | 0.9924 | 0.7852 | 0.8621 | 0.8119 | 0.6456 | 0.6767 | 0.5949 | 0.4936 | 0.7441 |

FIG. 5

| config | value |
|---|---|
| optimizer | AdamW |
| base learning rate | 3e-4 |
| weight decay | 0.005 |
| optimizer momentum | beta1, beta2= 0.9, 0.999 |
| batch size | 4 |
| learning rate schedule | linear warmup cosine annealing |
| warmup epochs | 300 |
| total epochs | 3000 |
| augmentation | RangeScaleIntensity |

FIG. 6

| config | value |
|---|---|
| optimizer | AdamW |
| base learning rate | 3e-4 |
| weight decay | 0.005 |
| optimizer momentum | beta1, beta2= 0.9, 0.999 |
| batch size | 4 |
| learning rate schedule | linear warmup cosine annealing |
| warmup epochs | 100 |
| total epochs | 1000 |
| augmentation | NormalizedIntensity |

FIG. 7

| config | value |
|---|---|
| optimizer | AdamW |
| base learning rate | 3e-4 |
| weight decay | 0.005 |
| optimizer momentum | beta1, beta2= 0.9, 0.999 |
| batch size | 4 |
| learning rate schedule | linear warmup cosine annealing |
| warmup epochs | 300 |
| total epochs | 3000 |
| augmentation | RangeScaleIntensity |

FIG. 8

| Methods | Backbones | Brain Tumor Sementation | | | Avg. ↑ |
|---|---|---|---|---|---|
| | | TC | WT | ET | |
| Sup. baseline | ViT3D-B | 0.8162 | 0.8781 | 0.5734 | 0.7559 |
| our impl. | ViT3D-L | 0.8178 | 0.8798 | 0.5745 | 0.7574 |
| SimCLR | ViT3D-B | 0.8360 | 0.8988 | 0.5869 | 0.7739 |
| | ViT3D-L | 0.8313 | 0.8944 | 0.5842 | 0.7699 |
| MAE | ViT3D-B | 0.8690 | 0.9340 | 0.6104 | 0.8045 |
| | ViT3D-L | 0.8723 | 0.9385 | 0.6130 | 0.8079 |
| SimMIM | ViT3D-B | 0.8734 | 0.9394 | 0.6103 | 0.8077 |
| | ViT3D-L | 0.8738 | 0.9401 | 0.6141 | **0.8093** |
| | Swn3D-S | 0.8428 | 0.9067 | 0.5922 | 0.7806 |
| | Swin3D-B | 0.8556 | 0.9205 | 0.6013 | 0.7924 |
| | VAN3D-B | 0.8406 | 0.9043 | 0.5907 | 0.7785 |
| | VAN3D-L | 0.8522 | 0.9169 | 0.5989 | 0.7893 |

FIG. 9

| Methods | Masked patch size | Masking ratio | Dice score Avg. ↑ |
|---|---|---|---|
| MAE | 16 | 0.15 | 0.7156 |
| | 16 | 0.30 | 0.7114 |
| | 16 | 0.45 | 0.6896 |
| | 16 | 0.60 | 0.7153 |
| | 16 | 0.75 | 0.7183 |
| | 24 | 0.15 | 0.6471 |
| | 24 | 0.45 | 0.7123 |
| | 24 | 0.75 | **0.7244** |
| | 32 | 0.15 | 0.7065 |
| | 32 | 0.45 | 0.7184 |
| | 32 | 0.75 | 0.7048 |
| SimMIM | 16 | 0.15 | 0.7144 |
| | 16 | 0.30 | 0.7248 |
| | 16 | 0.45 | 0.7227 |
| | 16 | 0.60 | 0.7208 |
| | 16 | 0.75 | 0.7249 |
| | 24 | 0.15 | 0.7292 |
| | 24 | 0.45 | 0.7278 |
| | 24 | 0.75 | 0.7256 |
| | 32 | 0.15 | **0.7471** |
| | 32 | 0.45 | 0.7264 |
| | 32 | 0.75 | 0.7245 |

FIG. 11

| Methods | Masked patch size | Masking ratio | Dice score Avg. ↑ |
|---|---|---|---|
| MAE | 16 | 0.15 | 0.7864 |
| | 16 | 0.30 | 0.7854 |
| | 16 | 0.45 | 0.7902 |
| | 16 | 0.60 | 0.7965 |
| | 16 | 0.75 | **0.8045** |
| | 24 | 0.15 | 0.7412 |
| | 24 | 0.45 | 0.7947 |
| | 24 | 0.75 | 0.8041 |
| | 32 | 0.15 | 0.7823 |
| | 32 | 0.45 | 0.7819 |
| | 32 | 0.75 | 0.8041 |
| SimMIM | 16 | 0.15 | 0.7818 |
| | 16 | 0.30 | 0.7923 |
| | 16 | 0.45 | 0.7945 |
| | 16 | 0.60 | 0.8058 |
| | 16 | 0.75 | **0.8077** |
| | 24 | 0.15 | 0.7852 |
| | 24 | 0.45 | 0.7654 |
| | 24 | 0.75 | 0.7982 |
| | 32 | 0.15 | 0.7985 |
| | 32 | 0.45 | 0.7958 |
| | 32 | 0.75 | 0.7986 |

FIG. 12

| Resolutions (downsampled ratio) | Pretrain data | Labeled ratio | Dice avg. |
|---|---|---|---|
| (2.0x, 2.0x, 2.0x) | COVID19 + BTCV | 50% | 0.6919 |
| (2.0x, 2.0x, 2.0x) | COVID19 + BTCV | 100% | 0.7338 |
| (1.5x, 1.5x, 2.0x) | COVID19 + BTCV | 50% | 0.7024 |
| (1.5x, 1.5x, 2.0x) | COVID19 + BTCV | 100% | 0.7534 |
| (2.0x, 2.0x, 2.0x) | BTCV | 50% | 0.6552 |
| (2.0x, 2.0x, 2.0x) | BTCV | 100% | 0.7018 |
| (1.5x, 1.5x, 2.0x) | BTCV | 50% | 0.6814 |
| (1.5x, 1.5x, 2.0x) | BTCV | 100% | 0.7183 |

FIG. 13

MEDICAL IMAGING ANALYSIS USING SELF-SUPERVISED LEARNING

CROSS REFERENCE TO RELATED APPLICATIONS

This U.S. patent application claims priority under 35 U.S.C. § 119(e) to U.S. Provisional Application 63/333,495, filed on Apr. 21, 2022. The disclosure of this prior application is considered part of the disclosure of this application and is hereby incorporated by reference in its entirety.

TECHNICAL FIELD

This disclosure relates to medical imaging analysis using self-supervised learning.

BACKGROUND

Multi-dimensional medical images, such as three-dimensional (3D) medical images, provide enriched images of an interior body of a patient to assist in facilitating medical analysis, diagnosis, or treatment of the patient. Such medical images can be generated using different modalities including, for example, computed tomography (CT) or magnetic resonance imaging (MM).

SUMMARY

One aspect of the disclosure provides a computer-implemented method that when executed on data processing hardware causes the data processing hardware to perform operations that include obtaining a first training data set including a plurality of unannotated multi-dimensional medical images and executing a self-supervised masked image modeling (MIM) training process to pre-train an image encoder on the first training data set. The operations also include obtaining a second training data set including a plurality of annotated multi-dimensional medical images. Here, each annotated multi-dimensional medical image includes a plurality of image voxels each paired with a corresponding ground-truth label indicating a class the corresponding image voxel belongs to. The operations also include executing a supervised training process to train an image analysis model on the second training data set to teach the image analysis model to learn how to predict the corresponding ground-truth labels for the plurality of image voxels of each annotated multi-dimensional medical image. The image analysis model incorporates the pre-trained image encoder.

Implementations of the disclosure may include one or more of the following optional features. In some implementations, for each corresponding unannotated multi-dimensional medical image in the first training data set, executing the self-supervised MIM training process to pre-train the image encoder includes generating, using an image tokenizer configured to receive the corresponding unannotated multi-dimensional medical image as input, a sequence of discrete visual tokens characterizing the corresponding unannotated multi-dimensional medical image, dividing the corresponding unannotated multi-dimensional medical image into a plurality of image patches, and randomly masking a portion of the image patches divided from the corresponding unannotated multi-dimensional medical image. For each masked image patch, the operations also include generating, using the image encoder, an encoded hidden representation for the masked image patch, and based on the encoded hidden representation, generating, using a decoder, a corresponding predicted token. Here, the operations also include determining a training loss based on the predicted tokens generated for the masked image patches and corresponding visual tokens from the sequence of discrete visual tokens that are aligned with the masked image patches, and updating parameters of the image encoder based on the training loss. In these implementations, the image encoder may include a plurality of multi-head attention layers, and the decoder may include a plurality of multi-head attention layers. Additionally or alternatively, randomly masking the portion of the image patches includes randomly masking the portion of the image patches using one of a central region masking strategy, a block-wise masking strategy, or a uniformly random masking strategy using different masked patch sizes and masking ratios. A number of visual tokens in the sequence of discrete visual tokens may be equal to a number of image patches in the plurality of image patches.

In some examples, for each corresponding unannotated multi-dimensional medical image in the first training data set, executing the self-supervised MIM training process to pre-train the image encoder includes dividing the corresponding unannotated multi-dimensional medical image into a plurality of image patches, each image patch represented by a corresponding set of raw voxel values, and randomly masking a portion of the image patches divided from the corresponding unannotated multi-dimensional medical image. For each masked image patch, the operations also include generating, using the image encoder, an encoded hidden representation for the masked image patch, and based on the encoded hidden representation, generating, using a prediction head, predicted voxel values for the masked image patch. Here, the operations also include determining a training loss based on the predicted voxel values generated for the masked image patches and the corresponding sets of the raw voxel values that represent the masked image patches, and updating parameters of the image encoder based on the training loss. In these examples, the image encoder may include a plurality of multi-head attention layers, and the prediction head may include a single linear layer prediction head and is configured to generate the predicted voxel values from the encoded hidden representation without using a decoder. Additionally or alternatively, randomly masking the portion of the image patches includes randomly masking the portion of the image patches using one of a central region masking strategy, a block-wise masking strategy, or a uniformly random masking strategy using different masked patch sizes and masking ratios. In some implementations, the image analysis model includes a tumor segmentation model. In some examples, the image analysis model includes a multi-organ segmentation model.

Another aspect of the disclosure provides a system including data processing hardware and memory hardware in communication with the data processing hardware. The memory hardware stores instructions that when executed by the data processing hardware cause the data processing hardware to perform operations that include obtaining a first training data set including a plurality of unannotated multi-dimensional medical images and executing a self-supervised masked image modeling (MIM) training process to pre-train an image encoder on the first training data set. The operations also include obtaining a second training data set including a plurality of annotated multi-dimensional medical images. Here, each annotated multi-dimensional medical image includes a plurality of image voxels each paired with a corresponding ground-truth label indicating a class the corresponding image voxel belongs to. The operations also include executing a supervised training process to train an image analysis model on the second training data set to teach the image analysis model to learn how to predict the corresponding ground-truth labels for the plurality of image voxels of each annotated multi-dimensional medical image. The image analysis model incorporates the pre-trained image encoder.

This aspect may include one or more of the following optional features. In some implementations, for each corresponding unannotated multi-dimensional medical image in the first training data set, executing the self-supervised MIM training process to pre-train the image encoder includes generating, using an image tokenizer configured to receive the corresponding unannotated multi-dimensional medical image as input, a sequence of discrete visual tokens characterizing the corresponding unannotated multi-dimensional medical image, dividing the corresponding unannotated multi-dimensional medical image into a plurality of image patches, and randomly masking a portion of the image patches divided from the corresponding unannotated multi-dimensional medical image. For each masked image patch, the operations also include generating, using the image encoder, an encoded hidden representation for the masked image patch, and based on the encoded hidden representation, generating, using a decoder, a corresponding predicted token. Here, the operations also include determining a training loss based on the predicted tokens generated for the masked image patches and corresponding visual tokens from the sequence of discrete visual tokens that are aligned with the masked image patches, and updating parameters of the image encoder based on the training loss. In these implementations, the image encoder may include a plurality of multi-head attention layers, and the decoder may include a plurality of multi-head attention layers. Additionally or alternatively, randomly masking the portion of the image patches includes randomly masking the portion of the image patches using one of a central region masking strategy, a block-wise masking strategy, or a uniformly random masking strategy using different masked patch sizes and masking ratios. A number of visual tokens in the sequence of discrete visual tokens may be equal to a number of image patches in the plurality of image patches.

In some examples, for each corresponding unannotated multi-dimensional medical image in the first training data set, executing the self-supervised MIM training process to pre-train the image encoder includes dividing the corresponding unannotated multi-dimensional medical image into a plurality of image patches, each image patch represented by a corresponding set of raw voxel values, and randomly masking a portion of the image patches divided from the corresponding unannotated multi-dimensional medical image. For each masked image patch, the operations also include generating, using the image encoder, an encoded hidden representation for the masked image patch, and based on the encoded hidden representation, generating, using a prediction head, predicted voxel values for the masked image patch. Here, the operations also include determining a training loss based on the predicted voxel values generated for the masked image patches and the corresponding sets of the raw voxel values that represent the masked image patches, and updating parameters of the image encoder based on the training loss. In these examples, the image encoder may include a plurality of multi-head attention layers, and the prediction head may include a single linear layer prediction head and is configured to generate the predicted voxel values from the encoded hidden representation without using a decoder. Additionally or alternatively, randomly masking the portion of the image patches includes randomly masking the portion of the image patches using one of a central region masking strategy, a block-wise masking strategy, or a uniformly random masking strategy using different masked patch sizes and masking ratios. In some implementations, the image analysis model includes a tumor segmentation model. In some examples, the image analysis model includes a multi-organ segmentation model.

The details of one or more implementations of the disclosure are set forth in the accompanying drawings and the description below. Other aspects, features, and advantages will be apparent from the description and drawings, and from the claims.

DESCRIPTION OF DRAWINGS

FIG. 5 is a table illustrating dice scores for multi-organ segmented images using an image analysis model.

FIG. 6 is a table listing supplemental baseline settings for a supervised training process that trains the image analysis model of FIG. 1

FIG. 7 is a table listing supplemental baseline settings for a supervised training process that trains the image analysis model of FIG. 1.

FIG. 8 is a table listing pre-training settings for the self-supervised MIM training process of FIG. 1.

FIG. 9 is a table defining results of using a machine learning model on brain tumor segmentation images after being pre-trained using a Bra TS training dataset.

FIG. 11 is a table depicting an ablation study of applying different masked patch size and masking ratios on a multi-organ segmentation task.

FIG. 12 is a table depicting an ablation study of applying different masked patch size and masking ratios on a brain tumor segmentation task.

FIG. 13 is a table depicting results of pre-training an image encoder using a fixed patch size and fixed masking ratio.

Like reference symbols in the various drawings indicate like elements.

DETAILED DESCRIPTION

Figure 1:
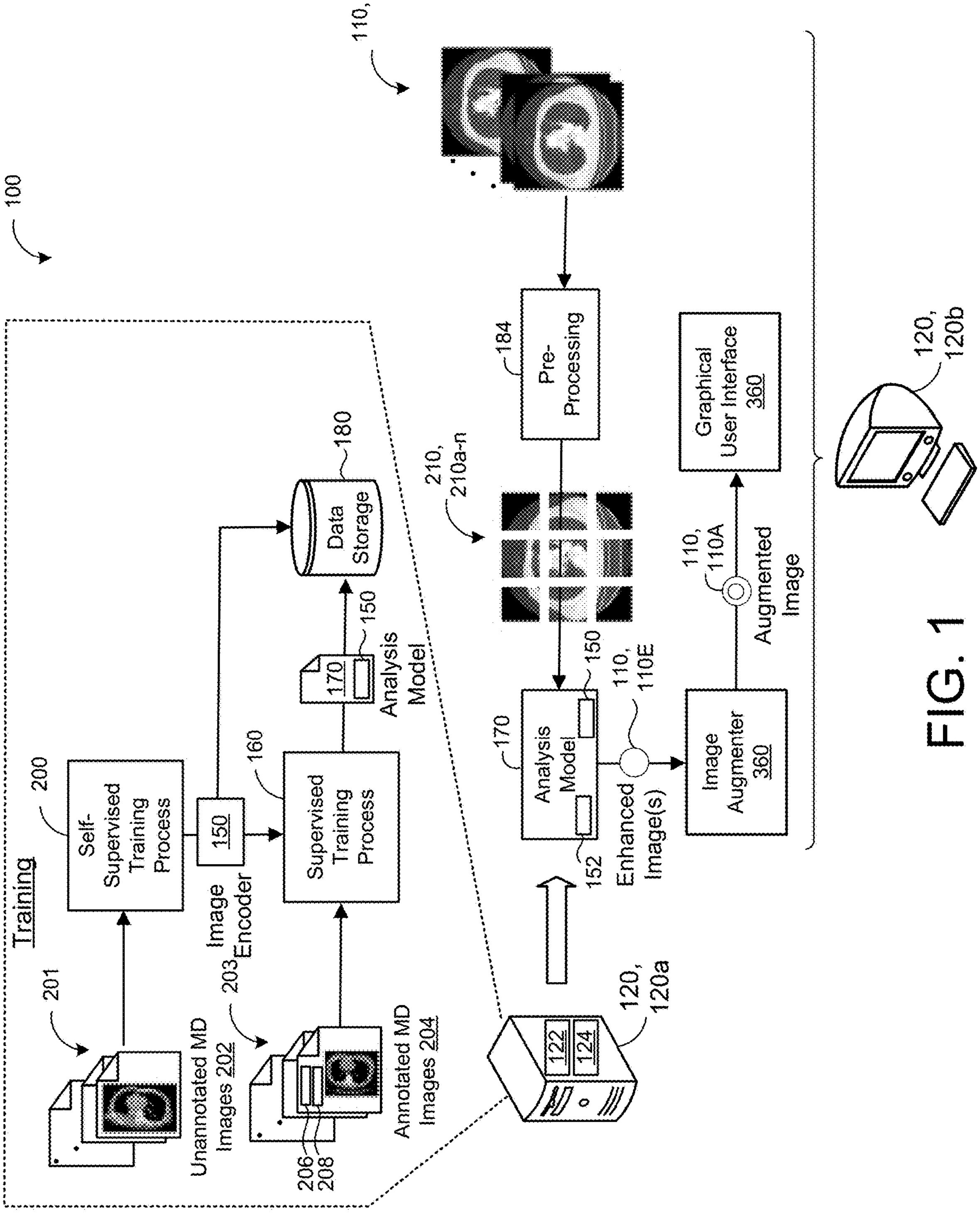
FIG. 1 is schematic view of a system for pre-training an image encoder using self-supervised masked image modeling (MIM) and training an image analysis model that incorporates the pre-trained image encoder.

Computer vision analysis has witnessed a paradigm shift from using Convolutional Neural Networks (CNNs) to using multi-head attention-based architectures. The present disclosure refers to Transformer-based architectures employing self-attention as one type of multi-head attention-based architecture by way of example, however, the present disclosure may employ other types of multi-head attention-based architectures for enhancing multidimensional input images. Generally, a Transformer-based architecture (i.e., a vision transformer) splits a multidimensional input image into patches and creates patch embeddings as inputs to a Transformer-based model for various vision tasks including image classification, object detection, and image segmentation.

Three-dimensional (3D) medical imaging technologies such as computed tomography (CT) or magnetic resonance imaging (MM) are widely used in diagnosing and treating a wide range of diseases. Generally, 3D medical volumetric images can help increase the speed and accuracy of diagnosing patient conditions. For instance, properly and swiftly discovering and measuring tumor lesions from MM or CT scans could be critical to disease prevention, early detection and treatment plan optimization, and also inspire the development of more successful clinical applications to ultimately improve patients' lives. A fundamental task performed for medical image analysis includes 3D image segmentation. Another fundamental task performed for medical image analysis includes image classification. Image classifications tasks classify input images into various categories. Generally, 3D image segmentation (also referred to as '3D semantic segmentation') aims to predict a corresponding class for each voxel of a volumetric input image to classify one or more particular objects and separating each of the particular objects from one another by overlying respective segmentation masks over the particular objects. 3D image segmentation has the potential to alleviate the burden for radiologists' daily workload by automating or assisting image interpretation workflow to ultimately improve clinical care and patient outcome. Example 3D image segmentation tasks may include multi-organ segmentation performed as a 13-class segmentation task with single-channel input and brain tumor segmentation performed as a three class segmentation class with four-channel input.

Training robust Transformer-based image analysis models require more annotated training data to surpass performance of conventional CNNs. However, the high expenses of obtaining expert annotations of 3D medical volumetric images in particular domains frequently stymies attempts to leverage advances in clinical outcomes using deep learning approaches for 3D medical image analysis. In short, annotations of 3D medical images at scale by radiologists are limited, expensive, and time-consuming to produce. Another limiting factor in 3D medical image processing is the sheer data volume associated with 3D medical images, which is driven by increased 3D image dimensionality and resolution, resulting in significant processing complexity. As a consequence, the ability to effectively integrate radiomics endpoint information with other bio-marker data for other downstream tasks in clinical study designs such as tumor burden assessment and overall survival prediction can be extremely difficult.

Transfer learning is the use of a trained model from one context in a different context. Transfer learning from natural images can be utilized in medical image analysis, regardless of disparities in image statistics, scale, and task-relevant characteristics. Transfer learning from, for example, ImageNet can accelerate convergence on medical images, which can be useful when the medical image training data is limited. Transfer learning using domain-specific data can also assist in resolving the domain disparity issue. For instance, improved performance can be achieved following pre-training on labeled data from the same domain. However, this strategy can be frequently impractical for a variety of medical scenarios requiring labeled data that is costly and time-consuming to gather. Self-supervised learning offers a viable alternative, allowing for the utilization of unlabeled/unannotated medical data.

Self-supervised learning is a training technique that focuses on learning representations from unlabeled data so that a low-capacity classifier can achieve high accuracy using various embeddings. Contrastive learning is another example of self-supervised learning strategies. Contrastive learning models image similarity and dissimilarity (or solely similarity) between two or more views, with data augmentation being crucial for contrastive and related approaches. Self-supervised learning can be used in the medical field such as in domain-specific pretext tasks or tailoring contrastive learning to medical data. A range of self-supervised learning strategies can be applied to 3D medical imaging. For example, a model pretrained on the ImageNet dataset can be applied to dermatology image classification. In another example, inpainting can be combined with contrastive learning for medical image segmentation.

Masked image modeling approaches, in general, mask out a portion of input images or encoded image tokens and encourage the model to recreate the masked area. Some extant MIM models employ an encoder-decoder design followed by a projection head. The encoder aids in the modeling of latent feature representations, while the decoder aids in the resampling of latent vectors to original images. The encoded or decoded embeddings can subsequently be aligned with the original signals at the masked area by a projection head. Notably, the decoder component can be a lightweight design so as to minimize training time. A lightweight decoder can not only reduce computing complexity but also can increase the encoder's ability to learn more generalizable representations that the decoder can easily grasp, translate, and convey. An encoder can be used for fine-tuning. Encoding techniques such as SimMIM can obviate the entire decoder with a single projection layer.

Using a vision transformer (ViT), for example, an image can be divided into regular non-overlapping patches (e.g., a 96×96×96 3D volume can be divided into 216 patches of 16×16×16 smaller volumes), which are often considered as the basic processing units of vision transformers. There are a number of random masking techniques, including but not limited to, a central region masking strategy, a complex block-wise masking strategy, and/or a uniformly random masking method at patch level using different masked patch sizes and masking ratios.

In some examples, the image encoder includes a vision transformer (ViT) architecture such as vanilla ViT (e.g., ViT3D, Swin-Transformer 3D, and/or an attention visual network (e.g., VAN3D) that can inherit an attention mechanism to derive hierarchical representations similar to, for example, Swin-Transformer 3D but instead using pure convolutions. Other types of multi-head attention layers may be employed by the image encoder such as, without limitation, Conformer layers, Performer layers, or lightweight convolutional layers.

Implementations herein are directed toward executing a self-supervised masked image modeling (MIM) training process to pre-train an image encoder on a plurality of unannotated (e.g., unlabeled) multi-dimensional medical images. As used herein, the multi-dimensional images are referred to as 3D medical images but may the disclosure is not so limited and may also include 4D medical images. The 3D medical images may include volumetric slices from CT or MM scans of interior (or exterior) body regions of patients. The image encoder includes a plurality of multi-head attention layers. For instance, the image encoder may include a Transformer-based architecture with self-attention that employs a stack of Transformer layers. As will become apparent, the image encoder is responsible for modeling latent feature representations of masked image patches, which can subsequently be utilized to forecast original image signals in regions associated with the masked image patches. The image encoder pre-trained on the unannotated 3D medical images via the self-supervised MIM training process is capable of adapting to a wide range of downstream vision tasks such as 3D image segmentation and image classification.

The pre-trained image encoder may be integrated into an image analysis model and fine-tuned using annotated multi-dimensional medical images to perform a particular downstream vision task. The annotated multi-dimensional medical images used to fine-tune the pre-trained image encoder, and ultimate train the image analysis model to perform the particular vision task, may each include a plurality of image voxels each paired with a corresponding ground-truth label indicating a class the corresponding image voxel belongs to. In this way, implementations of the present disclosure are further directed toward executing a supervised training process to train the image segmentation model on the plurality of annotated multi-dimensional medical images to teach the image segmentation model to learn how to predict the corresponding ground-truth labels for the plurality of image voxels for each annotated multi-dimensional medical image, whereby the image segmentation model includes the pre-trained image encoder initialized on the unannotated multi-dimensional images via the self-supervised MIM training process and fine-tuned on the annotated multi-dimensional images via the supervised training process. In some examples, the trained image analysis model includes an image segmentation model for performing 3D image segmentation tasks such as multi-organ segmentation or tumor segmentation performed on 3D image slices divided from MM or CT scans of interior body regions. Described in greater detail below, the trained image analysis model may receive, as input, multiple image patches divided from a multi-dimensional medical image (i.e., a volumetric slice from a MM or CT scan), generate an enhanced medical image based on features extracted from the multi-dimensional medical image, and perform image segmentation or image classification on the enhanced image. In the image segmentation scenario, the trained image analysis model may be trained to classify one or more particular objects (e.g., tumors or organs) in the enhanced image and separating each of the particular objects from one another by augmenting the enhanced image to include respective segmentation masks overlaying the particular objects. As used herein, augmenting an enhanced image to include a segmentation mask includes augmenting image voxels in the enhanced image that that represent each object class and/or define a boundary of the respective object class. The augmenting of image voxels may include changing a color of the image voxels, adjusting an intensity of the image voxels, or augmenting the image voxels in any suitable manner so that the each object classified is distinguishable and identifiable within the enhanced image.

FIG. 1 shows an example system 100 for pre-training an image encoder 150 via a self-supervised training process 200 to learn how to generate encoded feature representations 225 (FIGS. 2A and 2B) from unannotated 3D medical images 202 and fine-tuning the pre-trained image encoder 150 to perform a downstream image task via a supervised training process 160. Specifically, the pre-trained image encoder 150 may be adapted for use in an image analysis model 170 to perform a specific vision task by training the image analysis model 170 on annotated 3D medical images 204. The system 100 includes a computing system 120 having data processing hardware 122 and memory hardware 124 in communication with the data processing hardware 122 and storing instructions that cause the data processing hardware 122 to perform operations. In some implementations, a first computing system 120, 120*a* executes the self-supervised training process 200 to pre-train the image encoder 150 and then executes the supervised training process 160 to train the image analysis model 170 incorporating the pre-trained image encoder 150 to perform the downstream vision task on 3D medical images. In these implementations, after the image analysis model 170 is trained to perform the downstream vision task, the first computing system 120*a* may provide the trained image analysis model 170 to a second computing system 120, 120*b*. Here, the second computing system 120*b* may execute the image analysis model 170 to generate enhanced 3D medical images 110, 110E from raw 3D medical images 110, 110R and perform the downstream vision task on the enhanced 3D medical images 110E.

The first computing system 120*a* may include a distributed system (e.g., cloud computing environment). The second computing system 120*b* may include a computing device (e.g., desktop computer, workstation, laptop, tablet, etc.) that downloads the image analysis model 170 from the first computing system 120*a*. In some other implementations, the first computing system 120*a* receives the raw 3D medical images 110R from the second computing system 120*b* and executes the image analysis model 170 to perform the downstream vision task. In additional implementations, the second computing system 120*b* receives, from the first computing system 120*a*, the image encoder 150 pre-trained by the self-supervised training process 200 and executes the supervised training process 160 to fine-tune the pre-trained image encoder on the downstream vision task. In this scenario, the annotated MD images 204 may be processed locally on the second computing system 120*b* via the supervised training process 160, thereby preserving privacy and sensitive data.

The self-supervised training process 200 trains the image encoder 150 on a first training data set 201 that includes the plurality of unannotated multi-dimensional (MD) images 202. Specifically, and as described in greater detail below with reference to FIGS. 2A and 2B, the self-supervised training process includes a self-supervised masked image modeling (MIM) training process. Each unannotated MD image 202 in the first raining data set 201 may include an image slice divided from a CT scan or MRI scan of an interior body of a patient. Thus, the first training data set 201 may include a corpus of unannotated MD medical images 202 pertaining to image slices from CT scans and/or MRI scans of multiple patients' interior bodies. In one example, the first training data set 201 includes unannotated 3D CT scan images 202 obtained from The Cancer Imaging Archive-Covid 19 (TCIA-Covid19) public dataset. Here, the unannotated 3D CT scan images includes 771 volumes of unenhanced chest CT scans collected from 661 patients with Covid19 infections.

Notably, self-supervised MIM training as disclosed herein in is especially advantageous for modeling 3D medical images by significantly speeding up training convergence and improves downstream performance. For instance, when compared to naive contrastive learning, training convergence can save up to a 1.40× training cost to reach a same or higher dice score when the pre-trained image encoder 150 is adapted and fine-tuned to perform a downstream vision task. Similarly, the downstream performance of the downstream vision task of image segmentation can achieve over 5-percent (5%) improvements without any hyper parameter tuning. Additionally, downstream applications incorporating the image encoder pre-trained via self-supervised MIM training are faster and more cost-effective then transfer learning to the particular downstream task for prognosis, treatment sensitivity prediction, tissue segmentation, image classification, and digital representations of patients. As will become apparent, training the image encoder 150 via the self-supervised MIM training process 200 enables prediction of raw voxel values using a high masking ratio and a relatively small patch size. For simply reconstructing raw input 3D medical images 110R into enhanced 3D medical images 110E, a lightweight decoder may be implemented to receive the encoded feature representations 225 output by the image encoder 150 and perform reconstruction of image signals at increased speeds and reduced computing and memory costs. Self-supervised MIM training is versatile across raw input 3D medical images 110R having diverse image resolutions and labeled data ratios during the supervised training process 160.

Generally, MIM learning includes a learning task that includes masking a subset of input signals (e.g., image patches 210) and forecasting the masked signals. Stated differently, MIM learning/training is a self-supervised learning technique that learns representations via masking-corrupted images. Masking can be presented as a noise type. Masked patch prediction for self-supervised learning can predict missing voxels by inpainting a large rectangular area of the source areas and grouping voxel values into different clusters to classify unknown voxel values. Additionally, masked patch prediction for self-supervised learning can be accomplished by predicting a mean color of images.

After the image encoder 150 is pre-trained via the self-supervised training process 200, the supervised training process 160 trains the image analysis model 170 on a second training data set 203 that includes the plurality of annotated MD medical images 204. The supervised training process 160 fine-tunes the pre-trained image encoder 150 integrated with the image analysis model 170 to teach the image analysis model 170 to perform downstream vision tasks such as image segmentation tasks or image classification tasks. Each annotated MD medical image 204 includes a plurality of image voxels 206 each paired with a corresponding ground-truth label 208 indicating a class the corresponding image voxel 206 belongs to. Notably, the unannotated 3D images 202 in the first training data set 201 used to pre-train the image encoder 150 may be associated with a different medical domain than the annotated 3D images 204 in annotated second training data set 203. For instance, the first data set 201 may include chest CT scans while the second data set 203 may include abdominal CT scans or multimodal MRI scans of brain tumors.

The image analysis model 170 may include a U-shaped encoder-decoder architecture that includes the image encoder 150 (employed as a ViT-based encoder, Swin Transformer, or VAN) to produce hierarchical encoded features 225 (FIGS. 2A and 2B) from image patches 210 and a decoder 152. The decoder 152 may include a UPerNet to perform image segmentation tasks based on the encoded features 225 output from the image encoder 150. That is, a two-layer convolutional transpose can be used as a projection head 260 (FIG. 2A) during the self-supervised MIM training process 200 for pre-training the image encoder 150 and the UPerNet decoder 152 can be implemented for use with the pre-trained image encoder 150 by the image analysis model 170 for performing downstream image segmentation. In some examples, the image encoder 150 includes a masked audio encoder (MAE) (see FIG. 2A) employing a stack of multi-head attention layers. For instance, the MAE may include an 8-layer stack of Transformer blocks with 512-dimension for use by the decoder 152. In other examples, the image encoder includes a simple masked imaging model (SimMIM) (see FIG. 2B) and a single linear layer is used as a projection head in place of a decoder.

In one example, the second training data set 203 includes annotated 3D CT scans obtained from the Beyond the Cranial Vault (BTCV) Abdomen dataset that includes abdominal CT scans acquired from 30 participants/patients with 13 organ annotations by human interpreters under the supervision of clinical radiologists. Each 3D CT scan in the BTCV Abdomen dataset was performed in a portal venous phase with contrast enhancement and includes 80 to 225 slices with 512×512 pixels and a slice thickness ranging from one to six millimeters (mm). During pre-processing, each annotated 3D image 204 may be resampled to 1.5-2.0 isotropic voxel spacing. In this example, the supervised training process 160 trains the image analysis model 170 as a multi-organ segmentation model to perform 13-class segmentation with 1-channel output. Thus, the ground-truth label 208 for each corresponding image voxels 206 in each annotated 3D image 204 may include one of 13 different classes depending on which organ the corresponding image voxel 206 belongs to.

In another example, the second training data set 203 includes annotated 3D MRI scan images obtained from the Brain Tumor Segmentation (BraTS) public data set that includes multi-modal and multi-site MRI scans with the ground-truth labels 208 for corresponding image voxels 206 representing regions of edema, non-enhancing core, and necrotic core. In this example, the supervised training process 160 trains the image analysis model 170 as a brain tumor segmentation model to perform 3-class segmentation with 4-channel input. The voxel spacing of the Mill images can be 1.0×1.0×1.0 mm3. The voxel intensities can be pre-processed with z-score normalization.

The self-supervised training process 200 may store the pre-trained image encoder 150 in data storage 180 overlain on the memory hardware 124 of the computing system 120. Likewise, the supervised training process 160 may store the trained image analysis model 170 in the data storage 180. The first computing system 120*a* and/or any number of second computing systems 120*b* may access/retrieve the pre-trained image encoder 150 and/or the trained image analysis model 170 for execution thereon.

During inference, the image analysis model 170 incorporating the pre-trained and fine-tuned image encoder 150 executes on the second computing system 120*b* (or the first computing system 120*a*) to process and perform an image analysis task on one or more raw input 3D medical images 110R. Notably, the image analysis task performed by the image analysis model 170 includes the downstream vision task (i.e., image segmentation or image classification) the image analysis model 170 was trained by the supervised training process 160 to perform. Each raw input 3D medical image 110R may correspond to a 3D image slice from a 3D CT scan or an 3D MM scan of an interior body of a patient. Optionally, the raw input 3D medical images 110R may correspond to 3D images of an exterior body region of the patient. Each raw input 3D medical image 110R may undergo initial image pre-processing 184 to divide the raw input 3D medical image 110R into a plurality of image patches 210, 210*a*—n. While nine (9) image patches is shown by way of example, the example is non-limiting and the pre-processing 184 may divide the image into any number of image patches 210. The image analysis model 170 may process the image patches 210 to generate an enhanced 3D medical image 110E and perform the downstream vision task on the enhanced 3D medical images 110E. When the image analysis model 170 performs the downstream vision task of 3D image segmentation, the model 170 predicts a corresponding class for each voxel of the volumetric enhanced 3D medical image 110E to classify one or more particular objects (e.g., tumors, tissue, organs) and separates each of the particular objects from one another by defining a respective segmentation mask to overly the voxels classifying each object. Example 3D image segmentation tasks may include multi-organ segmentation performed as a 13-class segmentation task with single-channel input and brain tumor segmentation performed as a three class segmentation class with four-channel input.

An image augmenter 360 may receive the enhanced 3D medical image 110E segmented to identify the voxels that represent each particular object class and generate a corresponding segmentation mask to apply to at least a portion of the voxels representing the particular object class. Accordingly, the image augmenter 360 may augment image voxels in the enhanced image that represent each object class and/or define a boundary of the respective object class. The augmenting of image voxels may include changing a color of the image voxels, adjusting an intensity of the image voxels, or augmenting the image voxels in any suitable manner so that the each object classified is distinguishable and identifiable within the enhanced image 110E. The segmentation mask may include a a graphical feature applied to the enhanced image to convey the location of each object class identified in the enhanced image 110E. The image augmenter 360 may output an enhanced augmented image 110A depicting the segmentation masks convey the segmentation results performed by the analysis model 170. A graphical user interface 360 executing on the computing system 120 may display the augmented image 110A on a screen in communication of the computing system 120. Additionally or alternatively, the enhanced image and/or the augmented image 110A may be provided as output to one or more additional downstream tasks.

Figure 2A:
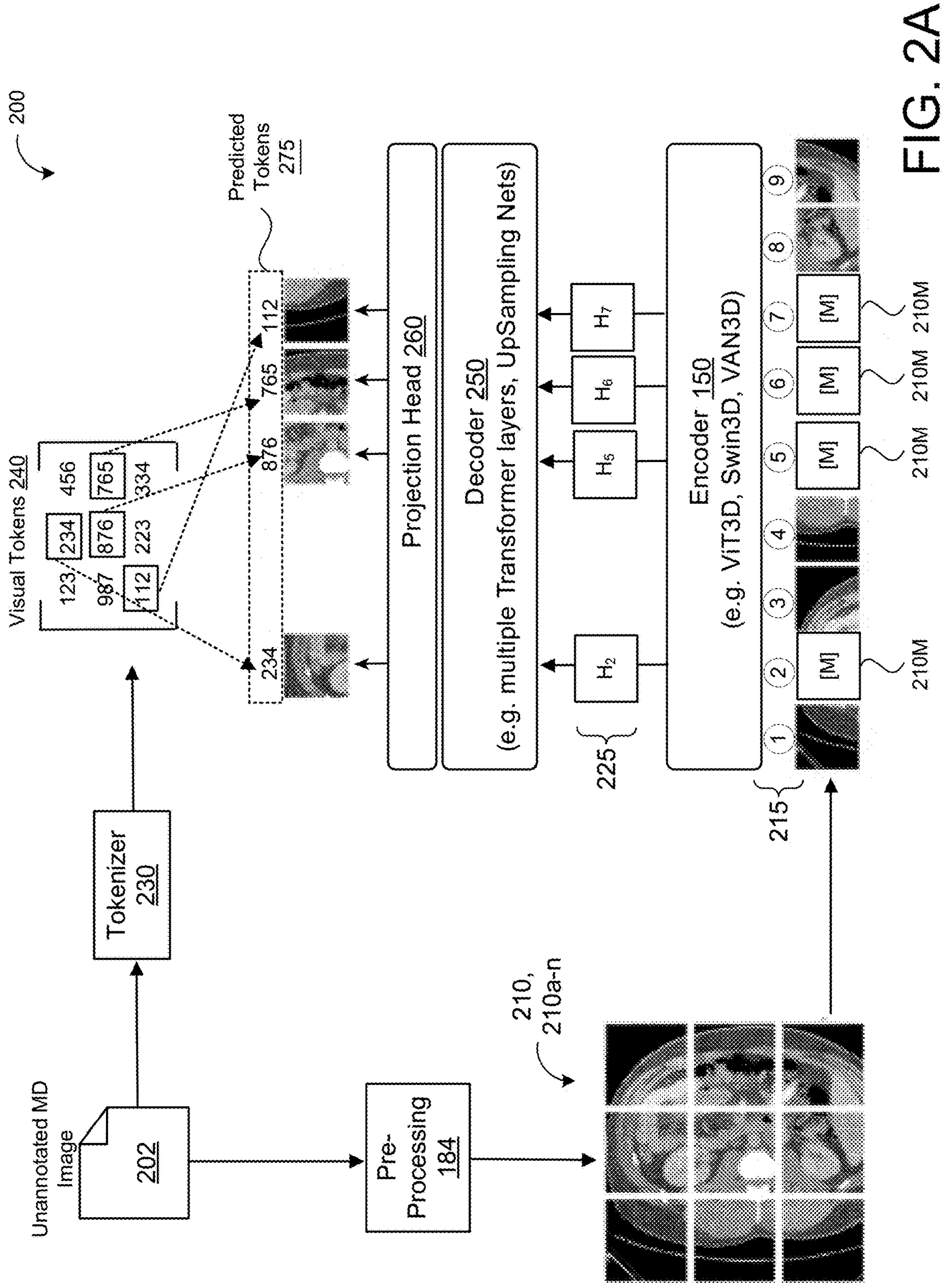
FIGS. 2A and 2B is a schematic view of example self-supervised MIM training processes for pre-training the image encoder of FIG. 1.
Figure 2B:
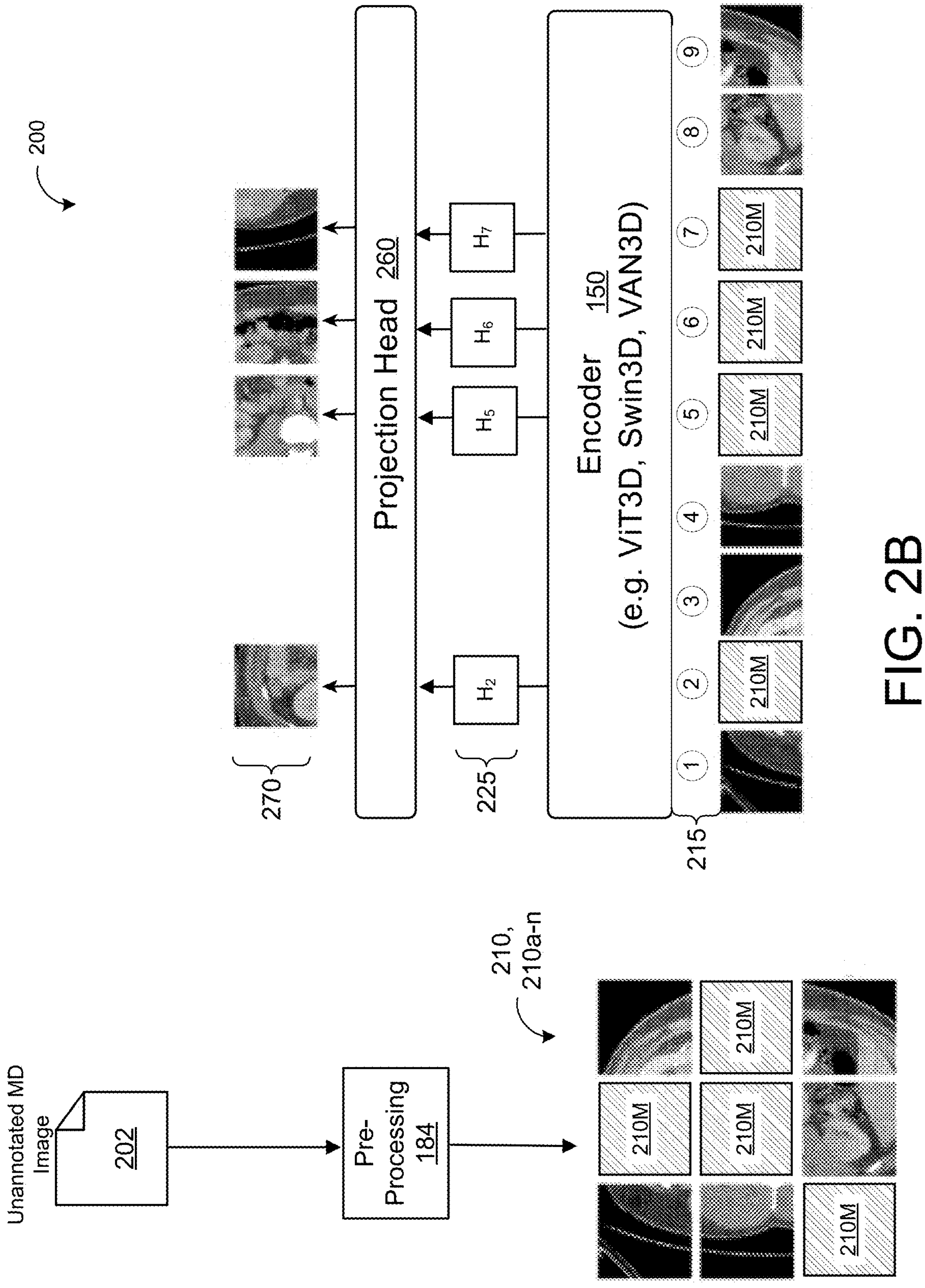

Referring to FIGS. 2A and 2B, in some implementations, the self-supervised MIM training process 200 pre-trains an image encoder 150 having either a masked autoencoder (MAE) architecture (FIG. 2A) or a simple MIM (SimMIM) architecture (FIG. 2B). For each unannotated 3D medical image 202, the training process 200 first pre-processes the image 202 at a pre-processing stage 184 to divide the image 202 into a plurality of image patches 210, 210*a-n*. As a full 3D image volume is typically difficult to load directly onto the data processing hardware (e.g., a GPU) 122 of the computing system 120, the self-supervised MIM training process 200 may implemented a sliding window training strategy in which the pre-processing divides the original 3D medical image 202 into several (e.g., 96×96×96) small 3D windows. By default, the pre-processing stage 184 may implement a patch size of about 16. The pre-processing stage may downsample image resolution of the unannotated 3D medical image 202. For instance, a 96× volume resolution can be downsampled to a 9× volume resolution when the image encoder 150 includes a ViT-based image encoder or can be downsampled to a 3× volume resolution when the image encoder 150 includes the SwinTransformer or VAN.

FIG. 2A shows the MIM training process 200 training the image encoder 150 having the MAE architecture by randomly masking a portion of the image patches 210 divided from a corresponding unannotated MD medical image 202. The training process 200 further randomly masks the portion of the image patches 210 by using one of a central region masking strategy, a block-wise masking strategy, or a uniformly random masking strategy that uses different masked patch sizes and masking ratios. The training process further generates, using an image tokenizer 230 configured to receive the unannotated MD medical image 202 as input, a sequence of discrete visual tokens 240 that characterize the corresponding unannotated MD medical image 202. The number of visual tokens in the sequence of discrete visual tokens 240 may be equal to the number of image patches 210 divided from the unannotated MD medical image 202. The tokenizer 230 may map discrete image voxels from the medical image 202 into the discrete visual tokens 240 according to a visual codebook that includes a token vocabulary containing discrete token indices. Since the visual tokens 240 are discrete, the training process 200 is non-differentiable. In some examples, the tokenizer 230 is trained via an autoencoding-style reconstruction process where images are tokenized into discrete visual tokens according to a learned vocabulary.

In the example shown, the self-supervised MIM training process 200 adds positional embeddings 215 to the image patches 210. The image encoder 150 receives each masked image patch 210M, whereby each masked image patch may be replaced with a special masking embedding [M]. The special masking token [M] may be randomly initialized as a learnable vector optimized to reveal the corresponding masked image patch 210.

For each masked image patch [M], the image encoder 150 is configured to generate a corresponding encoded feature representation 225 (also referred to as an encoded hidden representation 225) and a decoder 250 decodes the corresponding encoded feature representation 225 to predict a corresponding predicted token 275 as output from the projection head 260. The objective of the MIM training process 200 is to teach the image encoder 150 and the decoder 250 to learn how to predict the visual tokens 240 obtained from the original 3D image 202. Specifically, the training process 200 teaches the encoder 150 to produce encoded feature representations 225 for the masked image patches 210M for use in generating predicted tokens 275 that match the visual tokens 240 obtained from the original 3D image 202. Here, the training process 200 may determine a training loss based on the predicted tokens 275 generated for the masked image patches 210M and the corresponding visual tokens from the sequence of discrete visual tokens 240 that are aligned (i.e., using the positional embeddings 215) with the masked image patches 210M. Thereafter, the training process 200 updates parameters of the image encoder 150 (and optionally the decoder 250) based on the training loss.

The decoder may include a plurality of multi-head attention layers (e.g., Transformer layers). In some examples, the masked image patches 210M are invisible to the encoder 150, whereby only the decoder 250 has knowledge of the various tokens. This approach may save computation and memory while not interfering with training.

FIG. 2B shows the self-supervised MIM training process 200 training the image encoder 150 having the SimMIM architecture randomly masking a portion of the image patches 210 divided from a corresponding unannotated MD medical image 202. Each image patch 210 may be represented by a corresponding set of raw voxel values. The training process 200 further randomly masks the portion of the image patches 210 by using one of a central region masking strategy, a block-wise masking strategy, or a uniformly random masking strategy that uses different masked patch sizes and masking ratios.

In the example shown, the self-supervised MIM training process 200 adds positional embeddings 215 to the image patches 210. The image encoder 150 receives each masked image patch 210M, whereby each masked image patch may be replaced with a special masking embedding [M]. The special masking token [M] may be randomly initialized as a learnable vector optimized to reveal the corresponding masked image patch 210.

For each masked image patch 210M, the image encoder 150 is configured to generate a corresponding encoded feature representation 225 and a prediction head 260 generates predicted voxel values 270 for the masked image patch 210M. Notably, the MIM training process 200 for pre-training the image encoder 150 having the SimMIM architecture omits a decoder and instead implements a prediction head 260 to predict raw voxel values 270 for each masked image patch 210M directly from the encoded feature representation 225 generated by the image encoder 225 for the corresponding masked image patch 210M. The training process 200 may determine a training loss based on the predicted voxel values 270 generated for the masked image patches and the corresponding sets of raw voxel values from the original unannotated MD medical image 202 that represent the masked image patches.

The training loss may be based on a distance in a voxel space between the recovered/estimated raw voxel values 270 and the original voxels from the corresponding sets of raw voxel values that represent the masked image patches. The training loss may include either an $l_1$ or $l_2$ loss function. Notably, the training loss may only be computed for the masked matches 210M to prevent the encoder 150 from engaging in self-reconstruction and potentially dominate the learning process and ultimately impeded knowledge learning. Thereafter, the training process 200 updates parameters of the image encoder 150 (and optionally the decoder 250) based on the training loss. The projection head can transform the predicted tokens 275 to the original voxel space when the pre-processing down samples the resolution of the medical image 202. Optionally, a two-layer convolutional transpose can up sample the compressed encoded feature representations 225 to the resolution of the original medical image 202.

Figure 3:
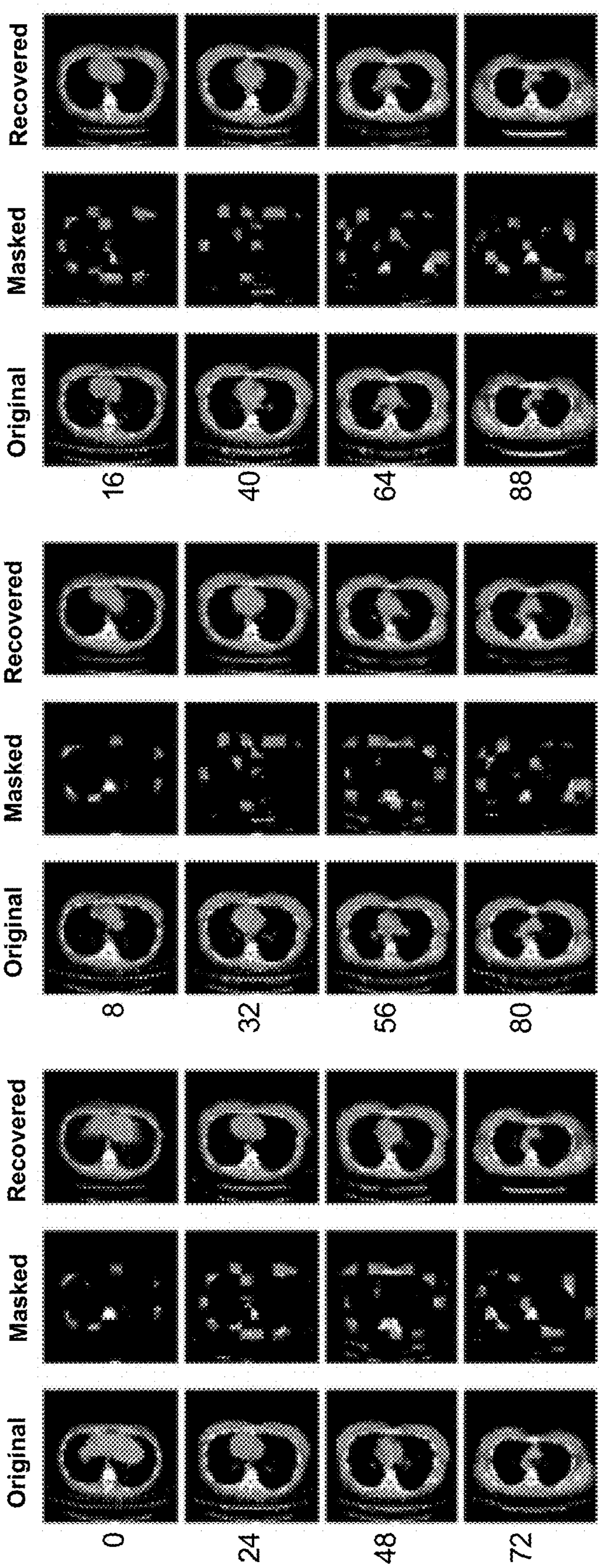
FIG. 3 illustrates example input, masked, and reconstructed 3D CT images using a pre-trained image encoder having a simple MIM architecture.

FIG. 3 illustrates example input, masked, and reconstructed 3D CT scan images from a TCIA-COVID19 validation set applying the pre-trained image encoder 150 using a SimMIM reconstruction. As the original images are all 3D volumes, the reconstructed images in the form of slices for the purpose of illustration and ease of understanding, where the indexing number represents the depth. For each triplet, the first or left most column illustrates the ground truth (e.g., original image). The second or middle column illustrates the masked image. The third column or right most column illustrates a machine learning model using a SimMIM reconstruction. For the images illustrated in FIG. 5, a ViT-Base backbone is applied for the encoder, the masked patch size is approximately 16 (for all dimensions), and the masking ratio is approximately 75%.

Figure 4:
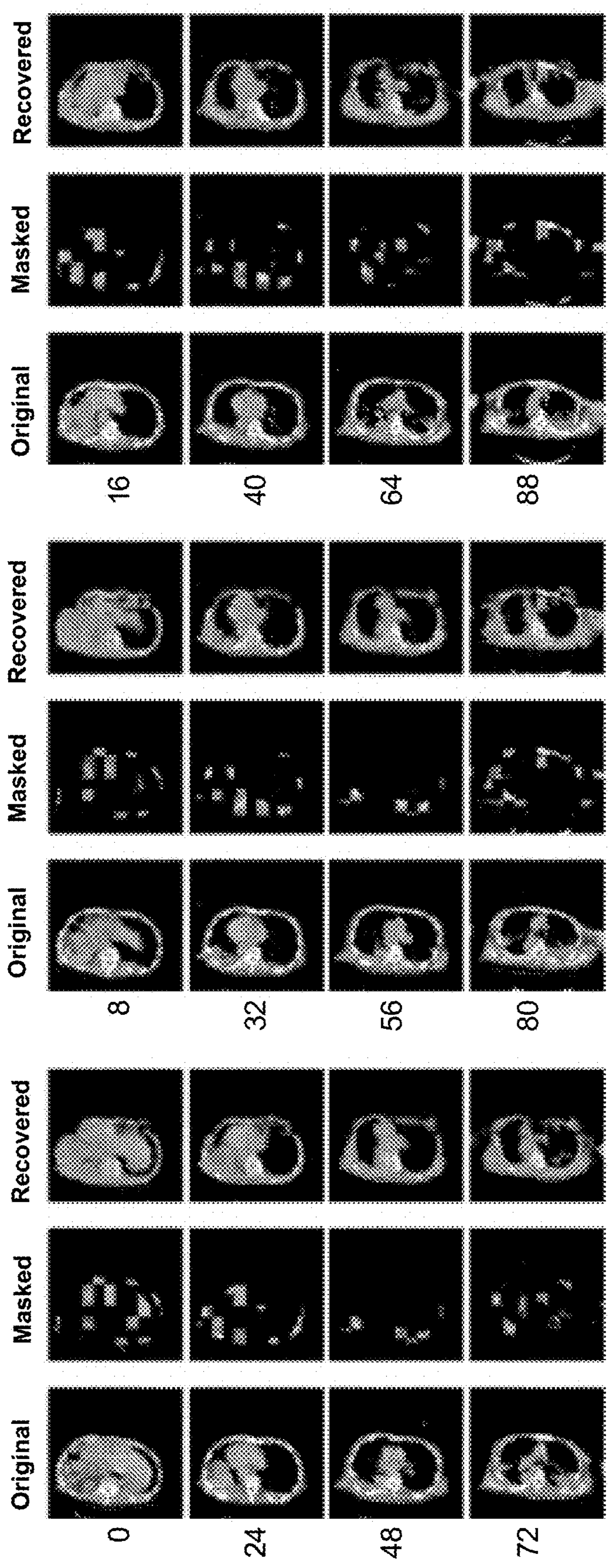
FIG. 4 illustrates example input, masked, and reconstructed 3D CT images using a pre-trained image encoder having a masked autoencoder (MAE) architecture.

FIG. 4 illustrates example input, masked, and reconstructed 3D CT scan images from a TCIA-COVID19 validation set applying a machine learning model using a MAE reconstruction. Similar to FIG. 3, as the original images are all 3D volumes, the reconstructed images in the form of slices for the purpose of illustration and ease of understanding, where the indexing number represents the depth. For each triplet, the first or left most column illustrates the ground truth (e.g., original image). The second or middle column illustrates the masked image. The third column or right most column illustrates a machine learning model using a MAE reconstruction. For the images illustrated in FIG. 4, a Vi T-Large backbone is applied for the encoder, the masked patch is approximately 16 (for all dimensions), and the masking ratio is approximately 75%.

FIG. 5 depicts a table demonstrating that MIM approaches can outperform contrastive learning techniques in general, as pre-trained image encoders 150 having both the MAE architecture and the SimMIM architecture achieved average dice scores of around 0.752 to 0.758, while SimCLR achieved an average dice score of about 0.723, which is 4.5% lower. As used herein, the Dice score is sued to evaluate an accuracy of segmentation performed as the downstream vision task. For a given semantic class, Gi and Pi denote ground truth and prediction values, respectively, for each corresponding voxel i. The following equation may be used to define the Dice score:

$$\text{Dice}\ (G, P) = \frac{2\sum_{i}^{I} G_i P_i}{\sum_{i=1}^{I} G_i + \sum_{i=1}^{I} P_i} \tag{1}$$

FIG. 6 includes a table listing supplemental baseline settings for the supervised training process 160 training the image analysis model 170 on the BTCV data set to perform multi-organ image segmentation. FIG. 7 includes a table listing supplemental baseline settings for the supervised training process 160 training the image analysis model 170 on the BraTS data set to perform brain tumor segmentation. FIG. 8 includes a table listing pre-training settings for the self-supervised MIM training process that uses 3D CT image volumes as the unannotated 3D medical images 202.

FIG. 9 shows is a table defining results of using a machine learning model on brain tumor segmentation images after being pre-trained using the Bra TS training dataset as the annotated MD medical images 204. The segmentation findings for BraTS in FIG. 8 follow a similar pattern as to the segmentation findings found in FIG. 5. The average dice score for masked image modeling approaches is somewhat greater than 0.80, however SimCLR obtains a dice value of 0.7739, which is 4.37% lower than the best approach comparable to FIG. 5. Another note is that, despite the similarity of the two MIM techniques, SimMIM can achieve slightly better performance than MAE, as demonstrated by both FIG. 5 and FIG. 9. One explanation for this is because an efficient decoder (even a lightweight one) may be able to reconstruct the original image even if the encoder 150 does not acquire generalizable representations, hence cyclically ease the motivation of encoder 150 to learn more effective representations 225. One goal of self-supervised MIM learning is to learn effective and generalizable representations of the data rather than self-convergence only. In comparison, SimMIM employs an even lighter design by omitting the decoder entirely, which pushes the encoder to perform more complex reconstruction and learning tasks.

Figure 10:
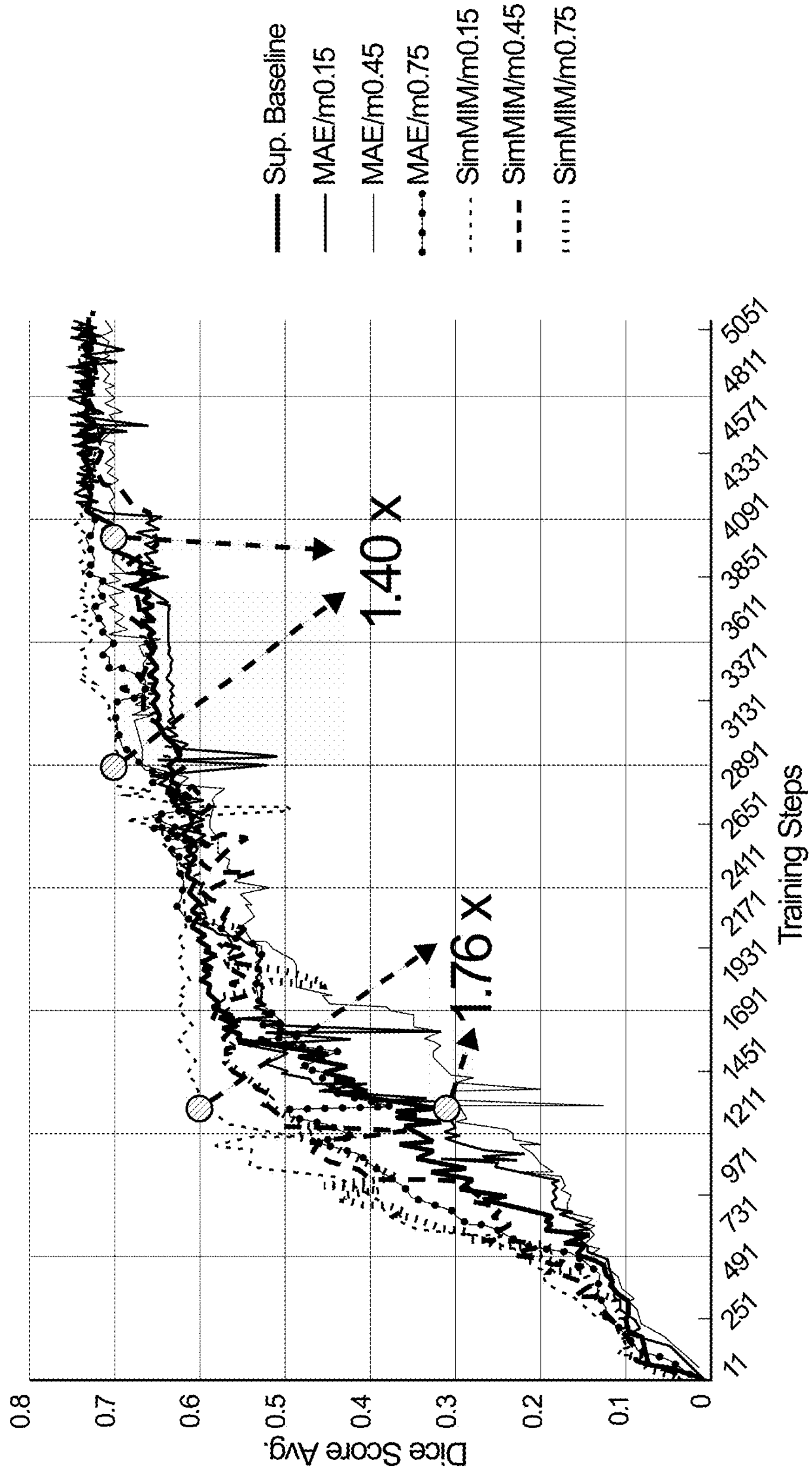
FIG. 10 is a plot depicting how self-supervised MIM training of an image encoder advances downstream supervised fine-tuning.

The self-supervised MIM training process 200 increases the training speed while reducing the cost to pre-train the image encoder 150 on the first training data set 201. FIG. 10 shows a plot depicting how the self-supervised MIM training process 200 advances the supervised training process 160. Here, an average dice score on a validation set is comparted between supervised baseline and different self-supervised MIM techniques using different masking ratios across training steps. Masked image modeling pre-training can save training costs and generate better performance. SimMIM based architectures can obtain a 1.76× better dice score at the 1.3 k training step. Moreover, MIM based approaches can reach a dice score of 0.7 with 1.4× less training time than the training time required for supervised baseline.

In some implementations, various masked patch sizes and masking ratios can be used for training the models using self-supervised MIM. Results of applying machine learning models to 3D medical images using several MIM techniques and then fine-tuning the pre-trained image encoder to perform downstream image segmentation are summarized in the tables of FIGS. 11 and 12. FIG. 11 includes a table depicting an ablation study of different masked patch size and masking ratio on multi-organ segmentation. The machine learning model 160 applied to generate the results in FIG. 13 had a default backbone of ViT-B applied as the pre-trained encoder 150. Additionally, the machine learning model 160 was trained via the supervised training process 160 using the BTCV training dataset. FIG. 12 is a table depicting an ablation study on different masked patch sizes and masking ratios on brain tumor segmentation. Likewise, the pretraining data includes the BraTS dataset itself and the ViT-B is applied as the encoder backbone in UNETR for segmentation fine-tuning.

A higher masking ratio is a non-trivial self-supervised learning job that can continually drive the model to build generalizable representations that can be transferred effectively to downstream tasks. For example, the best dice scores on multiorgan segmentation and brain tumor segmentation tasks are obtained when a masking ratio of approximately 0.75 is used across multiple patch sizes (e.g., 0.7183 for patch size 16 in FIG. 11, and 0.8041 for patch sizes 24 and 32 in FIG. 12). A high masking ratio combined with a small patch size results in a relatively good performance when used in conjunction with SimMIM. As illustrated in FIGS. 11 and 12, when the patch size is equal to 16, the models can perform with dice scores of approximately 0.7249 and 0.8077, respectively. However, as the patch size increases, the SimMIM method appears to be less sensitive to this masking ratio. For instance, when the patch size is approximately 32, models can earn the highest dice score with a masking ratio of approximately 0.15, the smallest possible masking ratio. Medical images are typically raw, low-level signals with a large degree of spatial redundancy and recovering some missing patches can be performed by directly copying nearby patches with little comprehensive knowledge of the objects and surroundings. A single small masked patch can be incapable of adequately masking complicated and intersecting structures or locations, but a high patch size may be able to hide more significant signals independently. As a result, a high masking ratio for small patch sizes can be more critical than a high masking ratio for larger patch sizes.

Generally, in supervised learning, more training data results in improved performance. FIG. 13 includes a table depicting Dice scores of an image analysis model 170 incorporating an image encoder 150 pre-trained via the self-supervised MIM training process 200 and hand having the MAE architecture (FIG. 2A). The image encoder 150 may be pre-trained on a variety of different data sources with varying degrees of down sampling. The supervised training process 160 may train the image analysis model 170 on the multi-organ segmentation dataset with varying labeled data ratios. The results of the table demonstrate that models trained on more plentiful unannotated 3D medical images 202 via the self-supervised MIM training process 200 outperform models trained on less unannotated 3D medical images, e.g., 0.7543 to 0.7184; 4.9% improvements and to 0.7018; 4.6% improvements). The advantage may be even more pronounced at lower image resolutions, as 0.6818 is 5.6% more than 0.6552 when only half-labeled data is used for supervised training.

FIG. 13 also depicts how different resolutions of the unannotated 3D medical images for pre-training affects the downstream image task performance. For example, a higher pre-training resolution may result in a better segmentation results, as the images contain more granular information. Here, different downsampled ratios can be used to represent the degree to which the original signals are compressed in all dimensions for each volume. As can be observed from FIG. 13, pre-trained encoder models with higher resolutions (e.g., 1.5×, 1.5×, 2.0×) generally perform better than pre-trained models with lower resolutions (e.g., 2.0×, 2.0×, 2.0×). For instance, 0.7338 dice score is 2.7% lower than the one pre-trained using the same data source and labeled ratio but using a greater resolution.

Figure 14:
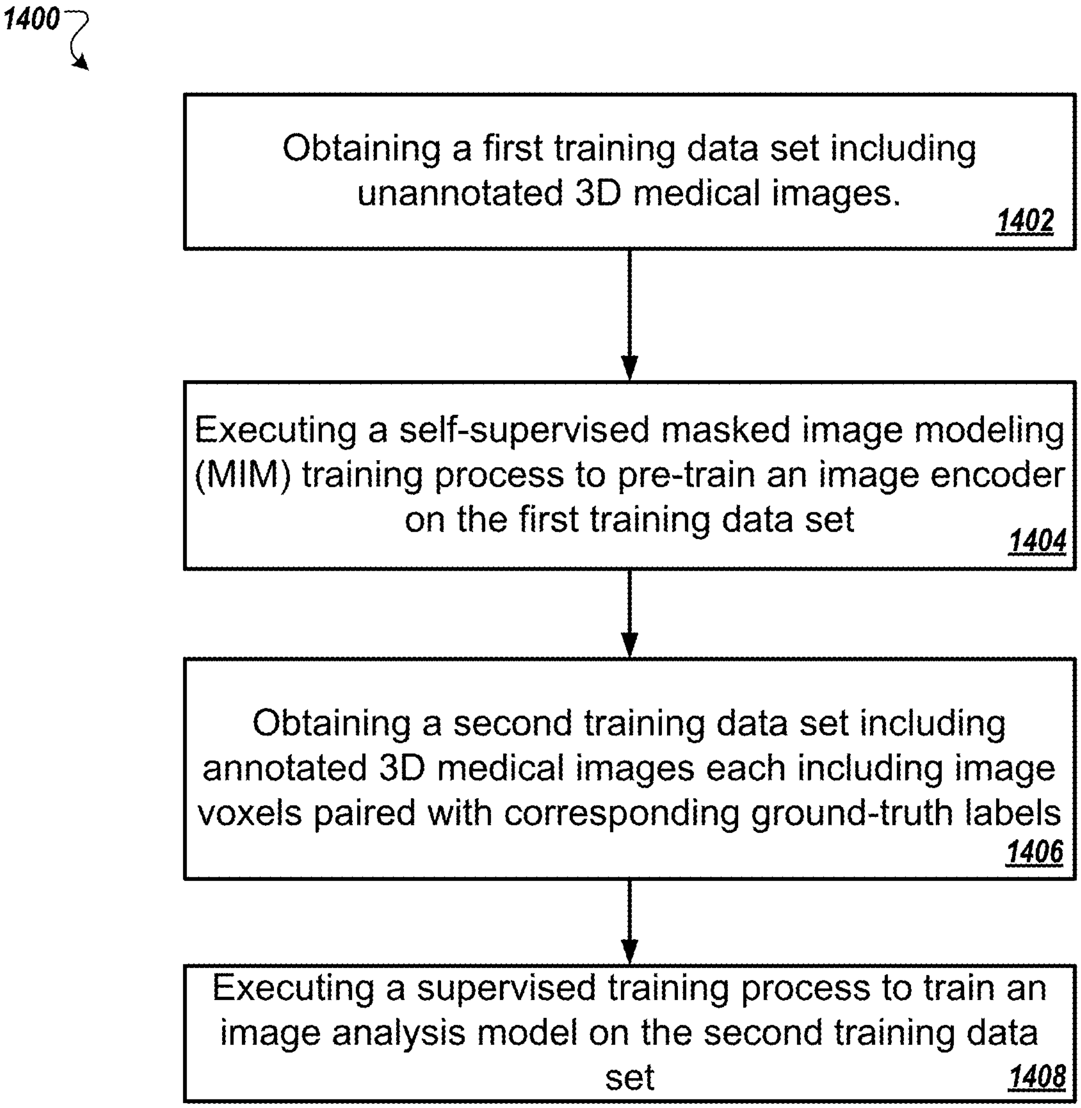
FIG. 14 is a flowchart of an example arrangement of operations for training an image analysis model to perform vision tasks on multi-dimensional medical images.

FIG. 14 is a flowchart of an example arrangement of operations for a method 1400 of training an image analysis model to perform image analysis tasks on multi-dimensional medical images. The data processing hardware 122 of the computing system 120 may execute instructions stored on the memory hardware 124 to perform the operations. At operation 1402, the method 1400 includes obtaining a first training data set 201 that includes a plurality of unannotated multi-dimensional medical images 202. At operation 1404, the method 1400 includes executing a self-supervised masked image modeling (MIM) training process 200 to pre-train an image encoder 150 on the first training data set 201.

At operation 1406, the method 1400 includes obtaining a second training data set 203 that includes a plurality of annotated multi-dimensional medical images 204. Here, each annotated multi-dimensional medical image 204 includes a plurality of image voxels 206 each paired with a corresponding ground-truth label 208 indicating a class the corresponding image voxel belongs to. At operation 1408, the method 1400 includes executing a supervised training process 160 to train the image analysis model 170 on the second training data set 203 to teach the image analysis model 170 to learn how to predict the corresponding ground-truth labels 208 for the plurality of image voxels 206 of each annotated multi-dimensional medical image 204. Here, the image analysis model 170 incorporates the pre-trained image encoder 150. The supervised training process 160 fine tunes the pre-trained image encoder 150 initialized via the self-supervised MIM training process 200.

A software application (i.e., a software resource) may refer to computer software that causes a computing device to perform a task. In some examples, a software application may be referred to as an "application," an "app," or a "program." Example applications include, but are not limited to, system diagnostic applications, system management applications, system maintenance applications, word processing applications, spreadsheet applications, messaging applications, media streaming applications, social networking applications, and gaming applications.

The non-transitory memory may be physical devices used to store programs (e.g., sequences of instructions) or data (e.g., program state information) on a temporary or permanent basis for use by a computing device. The non-transitory memory may be volatile and/or non-volatile addressable semiconductor memory. Examples of non-volatile memory include, but are not limited to, flash memory and read-only memory (ROM)/programmable read-only memory (PROM)/erasable programmable read-only memory (EPROM)/electronically erasable programmable read-only memory (EEPROM) (e.g., typically used for firmware, such as boot programs). Examples of volatile memory include, but are not limited to, random access memory (RAM), dynamic random access memory (DRAM), static random access memory (SRAM), phase change memory (PCM) as well as disks or tapes.

Figure 15:
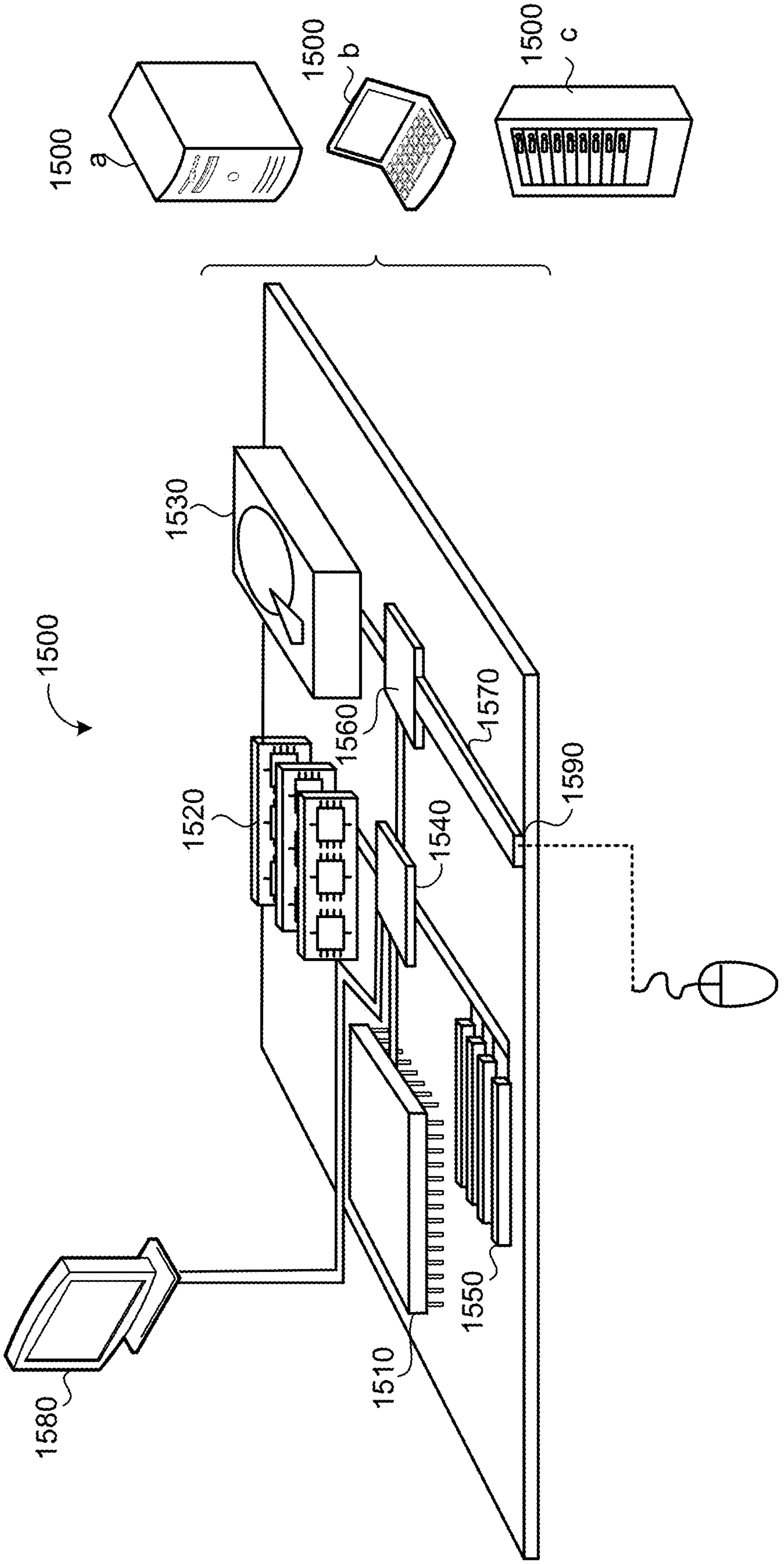
FIG. 15 is a schematic view of an example computing device that may be used to implement the systems and methods described herein.

FIG. 15 is schematic view of an example computing device 1500 that may be used to implement the systems and methods described in this document. The computing device 1500 is intended to represent various forms of digital computers, such as laptops, desktops, workstations, personal digital assistants, servers, blade servers, mainframes, and other appropriate computers. The components shown here, their connections and relationships, and their functions, are meant to be exemplary only, and are not meant to limit implementations of the inventions described and/or claimed in this document.

The computing device 1500 includes a processor 1510, memory 1520, a storage device 1530, a high-speed interface/controller 1540 connecting to the memory 1520 and high-speed expansion ports 1550, and a low speed interface/controller 1560 connecting to a low speed bus 1570 and a storage device 1530. Each of the components 1510, 1520, 1530, 1540, 1550, and 1560, are interconnected using various busses, and may be mounted on a common motherboard or in other manners as appropriate. The processor 1510 can process instructions for execution within the computing device 1500, including instructions stored in the memory 1520 or on the storage device 1530 to display graphical information for a graphical user interface (GUI) on an external input/output device, such as display 1580 coupled to high speed interface 1540. In other implementations, multiple processors and/or multiple buses may be used, as appropriate, along with multiple memories and types of memory. Also, multiple computing devices 1500 may be connected, with each device providing portions of the necessary operations (e.g., as a server bank, a group of blade servers, or a multi-processor system).

The memory 1520 stores information non-transitorily within the computing device 1500. The memory 1520 may be a computer-readable medium, a volatile memory unit(s), or non-volatile memory unit(s). The non-transitory memory 1520 may be physical devices used to store programs (e.g., sequences of instructions) or data (e.g., program state information) on a temporary or permanent basis for use by the computing device 1500. Examples of non-volatile memory include, but are not limited to, flash memory and read-only memory (ROM)/programmable read-only memory (PROM)/erasable programmable read-only memory (EPROM)/electronically erasable programmable read-only memory (EEPROM) (e.g., typically used for firmware, such as boot programs). Examples of volatile memory include, but are not limited to, random access memory (RAM), dynamic random access memory (DRAM), static random access memory (SRAM), phase change memory (PCM) as well as disks or tapes.

The storage device 1530 is capable of providing mass storage for the computing device 1500. In some implementations, the storage device 1530 is a computer-readable medium. In various different implementations, the storage device 1530 may be a floppy disk device, a hard disk device, an optical disk device, or a tape device, a flash memory or other similar solid state memory device, or an array of devices, including devices in a storage area network or other configurations. In additional implementations, a computer program product is tangibly embodied in an information carrier. The computer program product contains instructions that, when executed, perform one or more methods, such as those described above. The information carrier is a computer- or machine-readable medium, such as the memory 1520, the storage device 1530, or memory on processor 1510.

The high speed controller 1540 manages bandwidth-intensive operations for the computing device 1500, while the low speed controller 1560 manages lower bandwidth-intensive operations. Such allocation of duties is exemplary only. In some implementations, the high-speed controller 1540 is coupled to the memory 1520, the display 1580 (e.g., through a graphics processor or accelerator), and to the high-speed expansion ports 1550, which may accept various expansion cards (not shown). In some implementations, the low-speed controller 1560 is coupled to the storage device 1530 and a low-speed expansion port 1590. The low-speed expansion port 1590, which may include various communication ports (e.g., USB, Bluetooth, Ethernet, wireless Ethernet), may be coupled to one or more input/output devices, such as a keyboard, a pointing device, a scanner, or a networking device such as a switch or router, e.g., through a network adapter.

The computing device 1500 may be implemented in a number of different forms, as shown in the figure. For example, it may be implemented as a standard server 1500*a* or multiple times in a group of such servers 1500*a*, as a laptop computer 1500*b*, or as part of a rack server system 1500*c*.

Various implementations of the systems and techniques described herein can be realized in digital electronic and/or optical circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" and "computer-readable medium" refer to any computer program product, non-transitory computer readable medium, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

The processes and logic flows described in this specification can be performed by one or more programmable processors, also referred to as data processing hardware, executing one or more computer programs to perform functions by operating on input data and generating output. The processes and logic flows can also be performed by special purpose logic circuitry, e.g., an FPGA (field programmable gate array) or an ASIC (application specific integrated circuit). Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, one or more aspects of the disclosure can be implemented on a computer having a display device, e.g., a CRT (cathode ray tube), LCD (liquid crystal display) monitor, or touch screen for displaying information to the user and optionally a keyboard and a pointing device, e.g., a mouse or a trackball, by which the user can provide input to the computer. Other kinds of devices can be used to provide interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

A number of implementations have been described. Nevertheless, it will be understood that various modifications may be made without departing from the spirit and scope of the disclosure. Accordingly, other implementations are within the scope of the following claims.

What is claimed is:

1. A computer-implemented method executed on data processing hardware causes the data processing hardware to perform operations comprising:

obtaining a first training data set comprising a plurality of unannotated multi-dimensional medical images, wherein each unannotated multi-dimensional medical image among the plurality of unannotated multi-dimensional medical images comprises a corresponding three-dimensional medical image or a corresponding four-dimensional medical image;

executing a self-supervised masked image modeling (MIM) training process to pre-train an image encoder on the first training data set;

obtaining a second training data set comprising a plurality of annotated multi-dimensional medical images, each annotated multi-dimensional medical image comprising a plurality of image voxels each paired with a corresponding ground-truth label indicating a class the corresponding image voxel belongs to; and executing a supervised training process to train an image analysis model on the second training data set to teach the image analysis model to learn how to predict the corresponding ground-truth labels for the plurality of image voxels of each annotated multi-dimensional medical image, the image analysis model incorporates the pre-trained image encoder, wherein executing the self-supervised MIM training process to pre-train the image encoder comprises, for each corresponding unannotated multi-dimensional medical image in the first training data set:

generating, using an image tokenizer configured to receive the corresponding unannotated multi-dimensional medical image as input, a sequence of discrete visual tokens characterizing the corresponding unannotated multi-dimensional medical image;

dividing the corresponding unannotated multi-dimensional medical image into a plurality of image patches;

randomly masking a portion of the image patches divided from the corresponding unannotated multi-dimensional medical image by using one of a central region masking strategy, a block-wise masking strategy, or a uniformly random masking strategy using different masked patch sizes and masking ratios;

for each masked image patch:

generating, using the image encoder, an encoded hidden representation for the masked image patch; and based on the encoded hidden representation, generating, using a decoder, a corresponding predicted token;

determining a training loss based on the predicted tokens generated for the masked image patches and corresponding visual tokens from the sequence of discrete visual tokens that are aligned with the masked image patches; and updating parameters of the image encoder based on the training loss.

2. The method of claim 1, wherein:

the image encoder comprises a plurality of multi-head attention layers; and the decoder comprises a plurality of multi-head attention layers.

3. The method of claim 1, wherein a number of visual tokens in the sequence of discrete visual tokens is equal to a number of image patches in the plurality of image patches.

4. A computer-implemented method executed on data processing hardware causes the data processing hardware to perform operations comprising:

obtaining a first training data set comprising a plurality of unannotated multi-dimensional medical images, wherein each unannotated multi-dimensional medical image among the plurality of unannotated multi-dimensional medical images comprises a corresponding three-dimensional medical image or a corresponding four-dimensional medical image;

executing a self-supervised masked image modeling (MIM) training process to pre-train an image encoder on the first training data set;

obtaining a second training data set comprising a plurality of annotated multi-dimensional medical images, each annotated multi-dimensional medical image comprising a plurality of image voxels each paired with a corresponding ground-truth label indicating a class the corresponding image voxel belongs to; and executing a supervised training process to train an image analysis model on the second training data set to teach the image analysis model to learn how to predict the corresponding ground-truth labels for the plurality of image voxels of each annotated multi-dimensional medical image, the image analysis model incorporates the pre-trained image encoder, wherein executing the self-supervised MIM training process to pre-train the image encoder comprises, for each corresponding unannotated multi-dimensional medical image in the first training data set:

dividing the corresponding unannotated multi-dimensional medical image into a plurality of image patches, each image patch represented by a corresponding set of raw voxel values;

randomly masking a portion of the image patches divided from the corresponding unannotated multi-dimensional medical image;

for each masked image patch:

generating, using the image encoder, an encoded hidden representation for the masked image patch; and based on the encoded hidden representation, generating, using a prediction head, predicted voxel values for the masked image patch;

determining a training loss based on the predicted voxel values generated for the masked image patches and the corresponding sets of the raw voxel values that represent the masked image patches; and updating parameters of the image encoder based on the training loss.

5. The method of claim 4, wherein:

the image encoder comprises a plurality of multi-head attention layers; and the prediction head comprises a single linear layer prediction head and is configured to generate the predicted voxel values from the encoded hidden representation without using a decoder.

6. The method of claim 4, wherein randomly masking the portion of the image patches comprises randomly masking the portion of the image patches using one of a central region masking strategy, a block-wise masking strategy, or a uniformly random masking strategy using different masked patch sizes and masking ratios.

7. The method of claim 1, wherein the image analysis model comprises a tumor segmentation model.

8. The method of claim 1, wherein the image analysis model comprises a multi-organ segmentation model.

9. A system comprising:

data processing hardware; and memory hardware in communication with the data processing hardware and storing instructions that when executed on the data processing hardware causes the data processing hardware to perform operations comprising:

obtaining a first training data set comprising a plurality of unannotated multi-dimensional medical images, wherein each unannotated multi-dimensional medical image among the plurality of unannotated multi-dimensional medical images comprises a corresponding three-dimensional medical image or a corresponding four-dimensional medical image;

executing a self-supervised masked image modeling (MIM) training process to pre-train an image encoder on the first training data set;

obtaining a second training data set comprising a plurality of annotated multi-dimensional medical images, each annotated multi-dimensional medical image comprising a plurality of image voxels each paired with a corresponding ground-truth label indicating a class the corresponding image voxel belongs to; and executing a supervised training process to train an image analysis model on the second training data set to teach the image analysis model to learn how to predict the corresponding ground-truth labels for the plurality of image voxels of each annotated multi-dimensional medical image, the image analysis model incorporates the pre-trained image encoder, wherein executing the self-supervised MIM training process to pre-train the image encoder comprises, for each corresponding unannotated multi-dimensional medical image in the first training data set:

generating, using an image tokenizer configured to receive the corresponding unannotated multi-dimensional medical image as input, a sequence of discrete visual tokens characterizing the corresponding unannotated multi-dimensional medical image;

dividing the corresponding unannotated multi-dimensional medical image into a plurality of image patches;

randomly masking a portion of the image patches divided from the corresponding unannotated multi-dimensional medical image by using one of a central region masking strategy, a block-wise masking strategy, or a uniformly random masking strategy using different masked patch sizes and masking ratios;

for each masked image patch:

generating, using the image encoder, an encoded hidden representation for the masked image patch; and based on the encoded hidden representation, generating, using a decoder, a corresponding predicted token;

determining a training loss based on the predicted tokens generated for the masked image patches and corresponding visual tokens from the sequence of discrete visual tokens that are aligned with the masked image patches; and updating parameters of the image encoder based on the training loss.

10. The system of claim 9, wherein:

the image encoder comprises a plurality of multi-head attention layers; and the decoder comprises a plurality of multi-head attention layers.

11. The system of claim 9, wherein a number of visual tokens in the sequence of discrete visual tokens is equal to a number of image patches in the plurality of image patches.

12. A system comprising:
data processing hardware; and
memory hardware in communication with the data processing hardware and storing instructions that when executed on the data processing hardware causes the data processing hardware to perform operations comprising:
obtaining a first training data set comprising a plurality of unannotated multi-dimensional medical images, wherein each unannotated multi-dimensional medical image among the plurality of unannotated multi-dimensional medical images comprises a corresponding three-dimensional medical image or a corresponding four-dimensional medical image;
executing a self-supervised masked image modeling (MIM) training process to pre-train an image encoder on the first training data set;
obtaining a second training data set comprising a plurality of annotated multi-dimensional medical images, each annotated multi-dimensional medical image comprising a plurality of image voxels each paired with a corresponding ground-truth label indicating a class the corresponding image voxel belongs to; and
executing a supervised training process to train an image analysis model on the second training data set to teach the image analysis model to learn how to predict the corresponding ground-truth labels for the plurality of image voxels of each annotated multi-dimensional medical image, the image analysis model incorporates the pre-trained image encoder,
wherein executing the self-supervised MIM training process to pre-train the image encoder comprises, for each corresponding unannotated multi-dimensional medical image in the first training data set:
dividing the corresponding unannotated multi-dimensional medical image into a plurality of image patches, each image patch represented by a corresponding set of raw voxel values;
randomly masking a portion of the image patches divided from the corresponding unannotated multi-dimensional medical image;
for each masked image patch:
generating, using the image encoder, an encoded hidden representation for the masked image patch; and
based on the encoded hidden representation, generating, using a prediction head, predicted voxel values for the masked image patch;
determining a training loss based on the predicted voxel values generated for the masked image patches and the corresponding sets of the raw voxel values that represent the masked image patches; and
updating parameters of the image encoder based on the training loss.

13. The system of claim 12, wherein:
the image encoder comprises a plurality of multi-head attention layers; and
the prediction head comprises a single linear layer prediction head and is configured to generate the predicted voxel values from the encoded hidden representation without using a decoder.

14. The system of claim 12, wherein randomly masking the portion of the image patches comprises randomly masking the portion of the image patches using one of a central region masking strategy, a block-wise masking strategy, or a uniformly random masking strategy using different masked patch sizes and masking ratios.

15. The system of claim 9, wherein the image analysis model comprises a tumor segmentation model.

16. The system of claim 9, wherein the image analysis model comprises a multi-organ segmentation model.

* * * * *